May 5, 1959 E. S. BOERNER Plant Pat. 1,830
ROSE PLANT
Filed Oct. 20, 1958
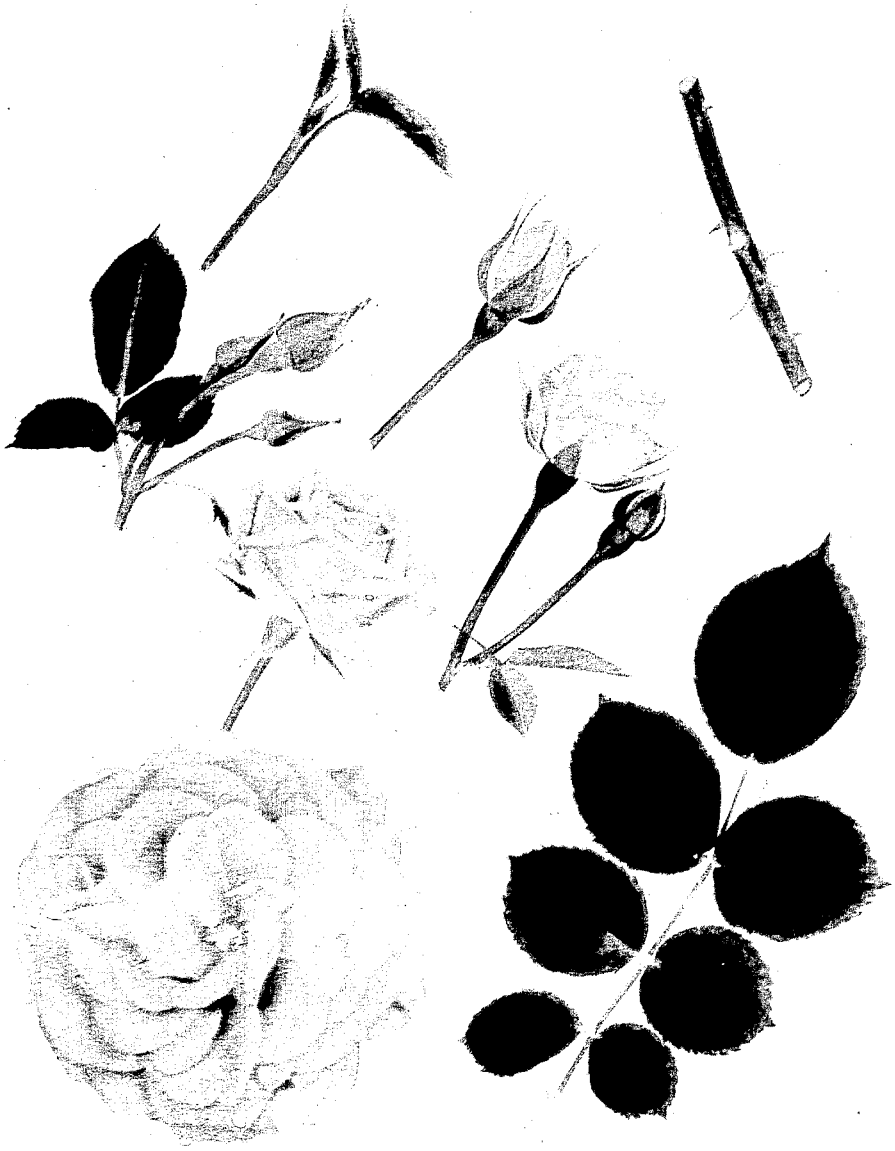
Inventor.
E. S. Boerner
By: Robert Robb
Attorneys.

United States Patent Office

Plant Pat. 1,830
Patented May 5, 1959

1,830

ROSE PLANT

Eugene S. Boerner, Newark, N.Y., assignor to Jackson & Perkins Company, Newark, N.Y., a corporation of New York Application October 20, 1958, Serial No. 768,505

1 Claim. (Cl. 47—61)

The present invention relates to a new and distinct variety of rose plant of the large-flowered polyantha class, which was originated by me by crossing the variety "Independence" (Plant Patent No. 1,036) with the variety "Fashion" (Plant Patent No. 789).

The primary objective of this breeding was to produce a new rose of the floribunda type corresponding to the parent varieties, but in which the plants are characterized by a freer blooming habit and more upright growth, as well as flowers of deeper color than those of "Fashion." This objective was fully achieved, along with other desirable improvements, including the attainment of flowers which have more petals per bloom than those of "Fashion."

The new variety is clearly differentiated from its parents as well as from all other varieties of which I am aware, as evidenced by the following unique combination of outstanding characteristics:

(1) Foliage which closely resembles that of the variety "Pinocchio" (Plant Patent No. 484), which is one of the distant parents;

(2) Freedom of bloom;

(3) Heavily flowered clusters;

(4) Long stems of the cluster shoots;

(5) Individual buds and flowers closely resembling those of the variety "Pinocchio"; and (6) A distinctive Begonia Rose, slightly overcast with Rose Doree, general color tonality of the flowers, which is different from any other floribunda in this general color range.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Independence."
*Pollen parent.*—"Fashion."
Classification:
*Botanic.*—Large-flowered polyantha.
*Commercial.*—Floribunda.

*Flower*

(Observations made from specimens grown in a greenhouse at Newark, New York, in the early afternoon during the latter part of March.)

Blooming habit: Recurrent—continuous.

Bud:
*Size.*—Medium.
*Form.*—Ovoid; is not affected by wet or hot weather.
*Color.*—When sepals first divide—Nopal Red, Plate 1. When petals begin to unfurl—Spectrum Red, Plate 1. When half-blown: inside of petals—Jasper Red, Plate 2, with outer edge of petal lightly overcast with Begonia Rose, Plate 1; reverse of petals—Rose Doree, Plate 1.
*Sepals.*—Slightly branched; curl back when petals begin to unfurl. Color: inside—Kildare Green, Plate 31; outside—Light Cress Green, Plate 31.
*Calyx.*—Color—Cress Green, Plate 31. Shape—pear. Size—small. Aspect—smooth. Odor when rubbed—none.
*Peduncle.*—Length — medium. Aspect — rough. Strength—erect; slender. Color—Light Cress Green, Plate 31.
*Opening.*—Opens up well; is not affected by adverse weather conditions.

Bloom:
*Size.*—Large. Average size when fully expanded—from 3½ inches to 4 inches.
*Borne.*—In irregular clusters.
*Stems.*—Medium length; strong.
*Form (when first open).*—Cupped. Permanence—flattens.
*Petalage.*—Double (full but open center). Number of petals under normal conditions—from 40 to 45.
*Color.*—Center of flower—Begonia Rose, Plate 1. Outer petals—Rose Doree, Plate 1. Base of petals (aiglet)—Citron Yellow, Plate 16. Inside of petals—Begonia Rose, Plate 1, slightly overcast with Rose Doree, Plate 1. Reverse of petals—Spinel Pink, Plate 26.
*General tonality from a distance.*—Begonia Rose, Plate 1.
*Discoloration.*—General tonality at end of first day—Rose Doree, Plate 1, with a slight overcast of Begonia Rose, Plate 1. General tonality at end of second day—Rose Doree, Plate 1, with a slight overcast of Begonia Rose, Plate 1. Third day—Begonia Rose, Plate 1.

Petals:
*Texture.*—Leathery; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; few; regularly arranged around styles. Color—Pinard Yellow, Plate 4.
Stamens, filaments (threads): Medium length. Color—Ochraceous-Buff, Plate 15.
Pollen: Color—Maize Yellow, Plate 3.
Styles: Loosely separated; uneven length; medium length; thin.
Stigmas: Color—Light Chalcedony Yellow, Plate 17.
Ovaries: All enclosed in calyx.
Hips: None.
Seeds: None.

*Plant*

Form: Bush.

Growth: Vigorous stems from 30 to 36 inches long; upright.

Foliage: Compound of 5 to 7 leaflets.

*Size.*—Medium.

*Quantity.*—Abundant.

*Color.*—New foliage: upper side—Parrott Green, Plate 6, with serrations of Victoria Lake, Plate 1; under side—Madder Brown, Plate 13. Old foliage: upper side—Varley's Green, Plate 18; under side—Light Cress Green, Plate 31.

*Shape.*—Oval pointed.

*Texture.*—Upper side—glossy. Under side—smooth.

*Ribs and veins.*—Ordinary.

*Edge.*—Serrated (saw-toothed).

*Serration.*—Both double and single; small.

*Leaf stem.*—Color—Absinthe Green, Plate 31. Under side—prickly.

*Stipules.*—Medium length; smooth.

Wood:

*New wood.*—Color—Rinnemann's Green, Plate 18. Bark—smooth.

*Old wood.*—Color—Bice Green, Plate 17. Bark—smooth.

Thorns:

*Thorns.*—Quantity: on main stalks from base—many; on laterals from stalk—many. Form—narrow base; medium length; hooked downward. Color (when young)—Eugenia Red, Plate 13.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of foliage closely resembling that of the variety "Pinocchio" (Plant Patent No. 484), freedom of bloom, heavily flowered clusters, long stems of the cluster shoots, individual buds and flowers closely resembling those of the variety "Pinocchio," and a distinctive Begonia Rose, slightly overcast with Rose Doree, general color tonality of the flowers.

No references cited.